United States Patent [19]

von Halasz

[11] 4,324,930
[45] Apr. 13, 1982

[54] 2,3-DICHLORO-2-TRIFLUOROMETHYL-1,1,1,3,4,4,5,5,5-NONAFLUOROPENTANE AND PROCESS FOR ITS MANUFACTURE

[75] Inventor: Sigmar-Peter von Halasz, Kelkheim, Fed. Rep. of Germany

[73] Assignee: Hoechst Aktiengesellschaft, Frankfurt am Main, Fed. Rep. of Germany

[21] Appl. No.: 247,787

[22] Filed: Mar. 26, 1981

[30] Foreign Application Priority Data

Mar. 28, 1980 [DE] Fed. Rep. of Germany ....... 3012005

[51] Int. Cl.$^3$ .................... B01J 19/08; C07C 19/08
[52] U.S. Cl. ...................... 570/134; 204/158 HA; 204/163 R
[58] Field of Search ............... 570/134, 123; 204/158 HA, 163 R

[56] References Cited

U.S. PATENT DOCUMENTS 2,407,246  9/1946  Benning et al. ............... 570/123
3,476,819  11/1969  Trischler ....................... 570/134

Primary Examiner—Howard S. Williams
Attorney, Agent, or Firm—Curtis, Morris & Safford

[57] ABSTRACT

The compound 2,3-dichloro-2-trifluoromethyl-1,1,1,3,4,4,5,5,5-nonafluoropentane is obtained by chlorinating perfluoro(2-methyl-2-pentene) with elementary chlorine in the presence of light rich in energy. This compound is distinguished by a high thermal and chemical stability.

1 Claim, No Drawings

2,3-DICHLORO-2-TRIFLUOROMETHYL-1,1,1,3,4,4,5,5,5-NONAFLUOROPENTANE AND PROCESS FOR ITS MANUFACTURE

The present invention relates to the novel compound 2,3-dichloro-2-trifluoromethyl-1,1,1,3,4,4,5,5,5-nonafluoropentane (I) and to a process for the manufacture thereof by photochlorination of perfluoro-2-methyl-2-pentene (II).

Perfluoro-2-methyl-2-pentene is readily accessible by dimerization of hexafluoropropene. Its reaction with elementary fluorine yielding perfluoro-2-methyl-pentane, a highly stable perhalogenated compound that can be used in many fields, is known from German Offenlegungsschrift No. 2,332,088.

This known process is disadvantageous in that the elementary fluorine used is expensive and not readily accessible.

It is the subject of the present invention to prepare a highly stable perhalogenated compound by using as starting compound perfluoro-2-methyl-2-pentene (II) without the use of elementary fluorine.

It has now been found that compound (I) is distinguished by a high thermal and chemical stability and that compound (I) can be obtained from (II) by means of chlorination.

Compound (I) is a colorless liquid having a boiling point of 112.5° C. It has the following consitution formula

$(CF_3)_2CCl-CClF-C_2F_5$

The process according to the invention for the manufacture of 2,3-dichloro-2-trifluoromethyl-1,1,1,3,4,4,5-5,5-nonafluoropentane (I) comprises reacting perfluoro-2-methyl-2-pentene (II) with elementary chlorine in the presence of light rich in energy at a temperature of from 20° to 300° C.

The process according to the invention may be carried out in continuous manner analogously to the known gas/gas reactions. A solid bed catalyst is not required. A temperature range of from 50° to 200° C. is preferred.

The components may alternatively be reacted in liquid phase, in batchwise or continuous manner. When working batchwise, compound II, in pure state or diluted by a solvent, is introduced initially into the reactor and elementary chlorine is added thereto subsequently. Suitable solvents are halogented hydrocarbons having a high boiling point, in particular the final product (I) of the process. The necessity of maintaining a liquid phase imposes an upper limit of temperature when working in this case at atmospheric pressure. The chlorination may alternatively be performed under elevated pressure, which, however, reduces the space/time yield.

A continuous operation mode is preferred, in which chlorine and the compound (II) are introduced simultaneously into a container filled with compound (I). Compound (II) should be at the boil or be kept at a temperature near the boiling point. A temperature of from 50° to 200° C. is preferred.

By "light rich in energy" there is to be understood a radiation which is capable of splitting up chlorine molecules into chlorine atoms, in particular visible light or ultraviolet light in a range of from 450 to 260 nm.

The process according to the present invention proceeds according to the following equation:

$(CF_3)_2C=CFCF_2CF_3 + Cl_2 \rightarrow$
$(CF_3)_2CClCClFCF_2CF_3$

The perfluoro-2-methyl-2-pentene (II) is used in technical-grade purity, advantageously in anhydrous form. It may be readily prepared by specific oligomerization of hexafluoropropene, which is available in technical-scale industry (for example according to Th. Martini and S. P. v. Halasz, Tetrahedron Letters 24, 2129-32 (1974). Elementary chlorine is taken from a commercial steel bottle and is used advantageously in anhydrous form, i.e. for example after having been dried with concentrated sulfuric acid.

The conversion rate of perfluoro-2-methyl-2-pentene at boiling temperature and atmospheric pressure depends on the radiation intensity and is in the range from about 0.5 to 4.0 mols/l of liquid phase and per hour.

Chlorine is generally used in an undiluted form, its quantity varies generally from 0.5 to 4.5 mols/l of liquid phase and hour. The quantity of chlorine should be at least equivalent to the quantity of perfluoro-2-methyl-2-pentene added simultaneously in continuous manner. A small chlorine excess is preferred. The molar ratio of the compound (II) to chlorine is preferably in the range of from 1:1 to 1:1.2, in particular of from 1:1 to 1:1.05.

Using a chlorine excess permits a quantitative conversion of perfluoro-2-methyl-2-pentene. A greater excess of chlorine is possible, but not advisable, since when using an efficient condensor the temperature in the liquid phase and thus of the reaction velocity may be reduced due to unreacted chlorine that liquifies at the condensor and flows back to the radiation reactor. A sub-stoichiometric quantity of chlorine can be used, but this leads to a reduction of the conversion rate and increases the expenditure during a subsequent working up. Excess chlorine is separated from the reaction product either by washing (with aqueous alkali metal hydroxide or thiosulfate) or advantageously by distillative working up.

The process of the invention is generally carried out without addition of an inert gas. Alternatively the gaseous feed products may be diluted with nitrogen or an other inert gas, with, however, does not bring about any advantage.

Reaction temperatures of from 60° to 120° C., especially of from 80° to 115° C., are preferred for the process of the invention. These temperatures may be easily maintained, in batchwise operation, by increasing the pressure, or, in the case of a continuous addtion, by heating the reaction medium. Suitable materials for the reactor are preferably light-permeable glass types, for example boron silicate glass.

The residence time of the low boiling starting products and of the higher boiling final products in the reactor is not critical, it may be, for example, for product (I), in the range from several hours to several days. The composition of the crude product is impaired in no case. An upper limit of the residence time is, however, given by economical consideratins, since a space-time yield as favorable as possible over a long test period is aimed at. In continuous operations, the addition of the starting products and the withdrawal of the final product are suitably controlled such that the level of the liquid phase in the radiation vessel remains approximately constant. Chlorine used in excess in the case of continuous operation may be recovered by distillative working up and be recycled to the reactor immediately. An advantage of this operation mode is to be seen in the high utilization of the feed products and in the extremely small quantities of waste water and of waste gas obtained.

The chlorination according to the invention is carried out generally under normal pressure, a reduced pressure or an elevated pressure being, however, likewise possible. For example, the pressure may be in the range of from 1 to 50, preferably 1 to 10, in particular 1 to 3, bar. An elevated pressure is advisable with a view to a higher space-time yield.

A conversion rate of perfluoro-2-methyl-2-pentene of more than 99% may be readily reached with the process according to the invention. Owing to the high selectivity of the process of the invention the yields of 2,3-dichloro-2-trifluoromethyl-nonafluoropentane (I) amount to about 98% of the theory. Products of the summation formula $C_{12}Cl_2F_{24}$ may be obtained in an amount of from 0.1 to 2% of the total yield, as a result of free radically initiated dimerization. These products have a varying constitution and boil at a temperature above 200° C. This simpliefies the distillative working up of the compound (I). For example, it is sufficient to work up the crude product by way of distillation, while removing the high boiling by-products, chlorine and the low boiling starting component (II).

The easily accessible compound (I) according to the process of the invention is a valuable product suitable for use as hydraulic fluid, as dielectric and as safety refrigerant, and especially for turbo-compressors, owing to its thermal and chemical stability, its inflammability and its exceptional physical, for example dielectric, properties. It is moreover suitable as heat transfer liquid in heat pumps, as working medium in expansion machines or as additive in fire extinguishers. The compound 2,3-dichloro-2-trifluoromethyl nonafluoropentane (I) may be used moreover as inert solvent or reaction medium, for example in halogenations. It is still further suitable as gentle solvent and degreasing agent in industrial cleaning operations, for example of construction materials and electric structural parts, in dry-cleaning of textile material or as additive to known cleansing agents.

The product of the invention has the advantage of having a high molecular weight of 371, which conditions a high boiling point and a relatively low vapor pressure, and of having a low solidification point of $-134°$ C. Its density is 1.830 g/cm$^3$ at 20° C. Moreover should be stressed the unexpectedly wide temperature range of the liquid phase of (I) reaching from $+112.5$ to $-134°$ C. under normal pressure. This range is considerably wider than that of the liquid phases of other industrially used halogenated hydrocarbons. Owing to these particular properties and in view of its viscosity behavior and its good miscibility with other chlorofluorohydrocarbons, the compound (I) is moreover suitable as lubricant, in particular in the field of the low temperature lubrication in cooling and air conditioning plants, which, as it is known, are operated with fluoro- or chlorofluorohydrocarbons. The compound (I) is moreover a valuable intermediate for the manfacture of further products, for example 2-chloro-2-trifluoromethyl-decafluoropentane, 3-chloro-2-trifluoromethyl-decafluoropentane and perfluoro-(2-methyl pentane), which compounds may be obtained by catalytic fluorination with hydrogen fluoride.

It is known from literature that the reactivity of oligomers of hexafluoropropene with respect to fluorine is drastically reduced with increasing branching of the carbon skeleton and with increasing molecular weight. Chlorinations of such oligomers have not been proposed hitherto. It is therefore surprising that the addition of chlorine to perfluoro-2-methyl-2-pentene according to the process of the invention can be carried out in such smooth manner and that it gives quantitative yields.

The invention will be illustrates, by way of example, in the following examples:

EXAMPLE 1

The test apparatus consists of a cylindrical multi-necked radiation flask of Duran$^{(R)}$ glass of 80 mm diameter and of a volume of about 2 liters. The glass vessel is equipped with an inner thermometer, a condensor charged with solid carbon dioxide and a delilvery cock located at its bottom. A gas inlet tube for compound (II) extends down to the lower third of the flask, but not to the bottom. The gas inlet tube for chlorine extends to the bottom of the flask. Two $^{(R)}$Ultra-Vitalux lamps of 300 watts are mounted outside of the glass vessel, one being directed towards the lower third of the height of the radiation vessel and the other one being directed towards the medium third of the height of the radiation vessel. These lamps simultaneously heat the radiation vessel. The upper outlet of the condensor is connected with a refrigerated condensation trap in which substances that may not have been retained by the condensor are collected.

Elementary chlorine is withdrawn from a commerical steel bottle, dried with concentrated sulfuric acid and introduced into the radiation flask, the feed being adjusted by means of a flow meter.

For photochlorination 2,000 g (6.67 mols) of compound (II) are placed into the radiation vessel and (at first) heated to a temperature of from 45° to 50° C. by the radiation lamps. After this temperature has been reached, elementary chlorine is introduced at a rate corresponding to its consumption during the reaction. A too rapid addition of chlorine results in a pronounced chlorine reflux at the condensor, liquified chlorine flows back and leads to an extreme cooling of the contents of the vessel, thus the conversion rate of chlorine per unit of time being still more reduced. At a temperature of from 20° to 50° C. there may be reacted a total of 260 g (3.66 mols) of chlorine, a further 218 g (3.07 mols) of chlorine being converted during a further 6.5 hours at a temperature above 50° C. The distillate is withdrawn upon completion of the reaction via the delivery cock at the bottom of the flask. Subsequently, the crude product obtained is analyzed by gas chromatography, which reveals the following composition:

97.8% of $(CF_3)_2CCl-CClF-CF_2-CF_3$
0.2% of $(CF_3)_2C=CF-CF_2-CF_3$
1.8% of isomer mixture of $C_{12}Cl_2F_{24}$ and
0.2% of other substances.

The raw product is worked up by distillation, whereupon compound (I) is obtained as colorless water-clear liquid boiling at 112.5° C./1 bar. Yield: 2,344 g, corresponding to 94.9% of the theory, relative to the converted product (II). A mixture consisting of various $C_{12}Cl_2F_{24}$ isomers that have been obtained by free radically initiated dimerization of the compound (II) is obtained in an amount of about 2%, relative to the total yield.

The compound I is identified by carbon, chlorine and fluorine analyses, which gave the following calculated data for $C_6Cl_2F_{12}$ (molecular weight 370.95): C 19.43%; Cl 19.11%; F 61.46%. Found: C 19.35%; Cl 19.5%; F 61.45%.

For the compound (I) there is determined a density of 1.830 g/cm$^3$ at 20° C. The solidification point is approximately −134° C. and the refractive index $n_D^{20°\,C.}$ is 1.323.

The infrared spectrum (liquid phase, capillary film) shows the expected main bands in the range of from 1,300 to 1,150 cm$^{-1}$ for $\nu_{C\text{-}F}$, at 955 cm$^{-1}$ for $\nu_{C\text{-}C}$ and at 733 and 695 cm$^{-1}$ for $\nu_{C\text{-}Cl}$.

The mass spectrum (measured by electron impact ionization) shows the characteristic fragments 335 m/e for (molecule—Cl)$^+$ of a relative intensity of about 1%, 251 m/e for (molecule—$C_2F_5$)$^+$ of a relative intensity of 10%, 185 m/e for $(CF_3CF_2CFCl)^{30}$ and/or $((CF_3)_2CCl)^+$ of a relative intensity of 55% and 69 m/e for $(CF_3)^+$ being the main peak (100% intensity).

In the $^{19}$F-NMR spectrum there can be found five types of fluorine nuclei of different nuclear magnetism, instead of four, owing to the asymmetric $C_3$ atoms. The resonance signals show the expected splitting and are centered at $\delta = -121.7$ ppm (CF), −116.6 ppm (CF$_2$), −78.0 ppm (CF$_3$) and at −66.0 and −65.2 ppm (the two non-identical CF$_3$ groups in $(CF_3)_2C$), relative to CCl$_3$F as internal standard.

EXAMPLE 2

The test apparatus of Example 1 is equipped with a further inlet (for the admission of compound (II)) which, like the inlet tube for chlorine, also extends down to the lower third of the volume of the radiation vessel, but not down to the bottom. In this example the compound (II) is initially placed in liquid state in a dropping funnel connected with the additionally mounted inlet tube, and not in the radiation flask.

The radiation flask is charged with 1,750 g (4.72 mols) of 2,3-dichloro-2-trifluoromethyl-nonafluoropentane (I) that has been prepared according to Example 1.

To effect the photochlorination of II, the initially placed compound (I) is heated to a temperature of 105° C. Subsequently there are added at a temperature of from 105° C. to 75° C. within 6.5 hours a total of 2,466 g (8.22 mols) of perfluoro-(2-methyl-2-pentene) (II) and 610 g (8.59 mols) of chlorine, corresponding to a molar ratio of the compound (II) to Cl$_2$ fo 1:1.045 mol, in continuous and uniformous manner at a rate of about 1.26 mols of the compound II/h and of 1.32 mols of Cl$_2$/h. The exposure to light is carried out as specified in Example 1. Compound I is withdrawn continuously during the test period through the delivery cock located at the bottom at a rate of from about 450 to 470 g/h. The volume of the contents of the flask remains approximately constant.

The following composition of the raw product obtained is determined by gas chromatographic analysis:

98.6% of $(CF_3)_2CCl\text{—}CClF\text{—}CF_2\text{—}CF_3$
1.1% of $(CF_3)_2C\text{=}CF\text{—}CF_2\text{—}CF_3$
0.3% of isomers of $C_{12}Cl_2F_{24}$.

A subsequent distillation yields compound (I) as a main fraction at 112.5° C. weighing 2,988 g (8.05 mols), corresponding to a yield of 99.0% of the theory, relative to converted compound (II).

What is claimed is:

1. The compound 2,3-dichloro-2-trifluoromethyl-1,1,1,-3,4,4,5,5,5-nonafluoropentane.

* * * * *